United States Patent [19]

Morris

[11] 4,185,625
[45] Jan. 29, 1980

[54] SURGICAL COVER SHEET

[75] Inventor: Henrietta K. Morris, Old Bridge, N.J.

[73] Assignee: Johnson & Johnson, New Brunswick, N.J.

[21] Appl. No.: 935,059

[22] Filed: Aug. 18, 1978

[51] Int. Cl.² ............................................. A61B 19/06
[52] U.S. Cl. .................................................. 128/132 D
[58] Field of Search ............................ 128/132 D, 292

[56] References Cited

U.S. PATENT DOCUMENTS

| | | | |
|---|---|---|---|
| 3,667,458 | 6/1972 | Krebs | 128/132 D |
| 3,721,234 | 3/1973 | Hadtke et al. | 128/132 D |
| 3,741,206 | 6/1973 | Binard et al. | 128/132 D |
| 3,791,381 | 2/1974 | Krzewinski | 128/132 D |
| 3,881,476 | 5/1975 | Bolker et al. | 128/132 D |
| 3,910,268 | 10/1975 | Miller | 128/132 D |
| 3,926,185 | 12/1975 | Krzewinski | 128/132 D |
| 3,952,738 | 4/1976 | Krzewinski | 128/132 D |
| 3,998,221 | 12/1976 | Collins | 128/132 D |

*Primary Examiner*—Lawrence W. Trapp

[57] ABSTRACT

A surgical cover sheet which can be used to cover a patient or operating room equipment such as an instrument table. The drape comprises a generally rectangular sheet of flexible, drapable material, preferably a nonwoven fabric, which is folded longitudinally to reduce its size. The longitudinally folded drape may be applied by a sterile or non-sterile nurse without contaminating an aseptic field. The longitudinally folded drape may be further folded in the transverse direction for packaging, sterilization and storage.

3 Claims, 16 Drawing Figures

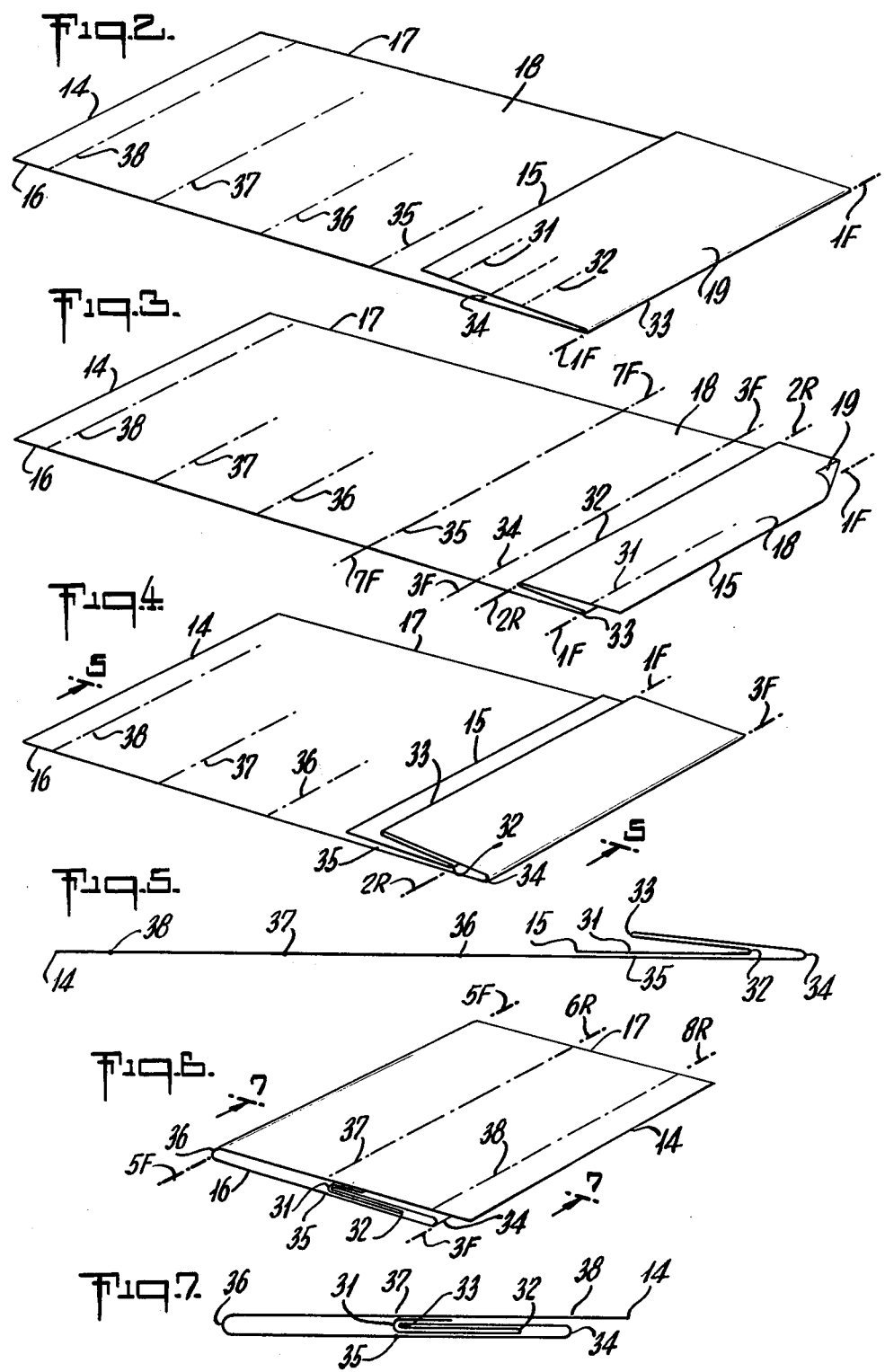

U.S. Patent   Jan. 29, 1980   Sheet 3 of 3   4,185,625
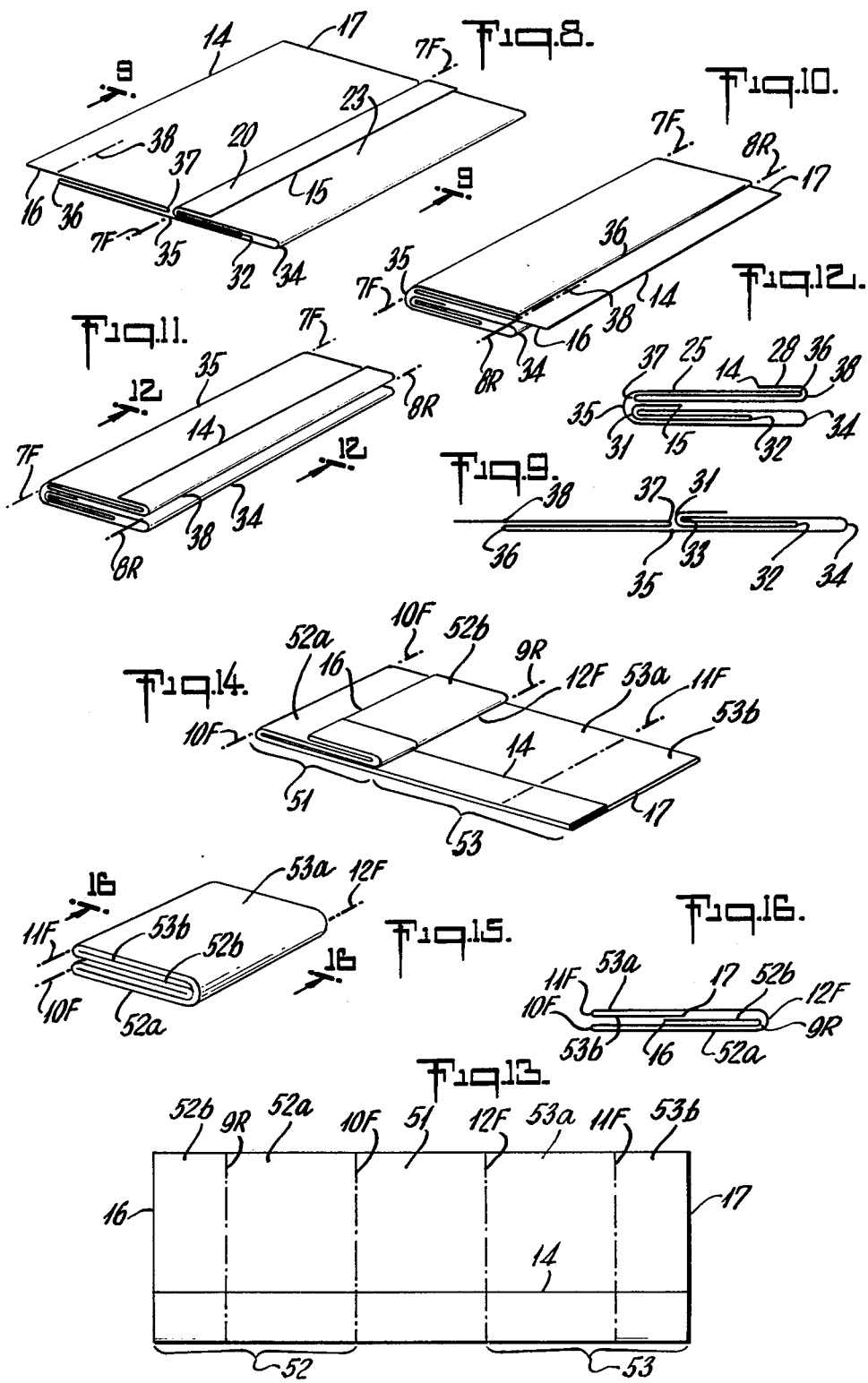

SURGICAL COVER SHEET

TECHNICAL FIELD

This invention relates to surgical cover sheets and especially to disposable folded surgical cover sheets which can be opened without danger of contaminating a sterile field by either a circulating (non-sterile) nurse or a scrub (sterile) nurse. Such cover sheets may be used to cover patients or auxiliary equipment, such as a back table, normally found in hospital operating rooms.

BACKGROUND ART

A quite large number of surgical cover sheets, often referred to as surgical drapes, are known in the art. Many of the drapes are folded in specific manner to provide compactness, or to facilitate their application to the patient, or to lessen the possibility that sterile fields (such as a surgically prepared portion of a patient's body) are not accidentally contaminated during the draping procedure, or to provide a sterile cover for a non-sterile surface.

U.S. Pat. No. 3,335,719 discloses a surgical legging having a cuff at the open end and folded so as to facilitate application of the drape to the leg of a patient.

U.S. Pat. No. 3,343,534 discloses a folded surgical drape comprising a first stack of folds overlying a second stack of folds.

U.S. Pat. No. 3,791,381 discloses a multipurpose reinforced surgical drape which is so folded that the reinforced portion of the drape may be cut to form functional drapes for various surgical procedures.

U.S. Pat. No. 3,910,268 discloses a surgical drape useful in orthopaedic and related surgery. The drape may be folded as described in the patent into a compact unit which permits it to be easily and quickly unfolded and applied to the patient prior to surgery.

U.S. Pat. No. 3,926,185 discloses several surgical drapes and methods for folding same into compact units.

U.S. Pat. No. 3,952,738 discloses a surgical drape useful for draping the patient's head during surgery involving the eyes, ears, nose and throat. The drape is shortened longitudinally by fan-folding and thereafter shortened transversely by first folding the end edges toward the center and then folding the drape in half.

U.S. Pat. No. 3,288,135 discloses a bifurcated surgical drape which is folded longitudinally along a line paralleling the upper edge of the drape. The drape may thereafter be folded along a second, vertically extending line joining the top and bottom edges.

U.S. Pat. No. 3,667,458 discloses a disposable, fenestrated surgical drape which is shortened longitudinally by fan-folding from the top and bottom ends toward the center to provide two stacks of folds. The drape is shortened transversely in the same manner.

U.S. Pat. No. 3,721,234 discloses a disposable fenestrated surgical cover sheet which is fan-folded inwardly from its longitudinal and transverse edges to produce a compact, generally rectangular package.

U.S. Pat. No. 3,741,206 discloses a fenestrated drape in which a pair of longitudinally extending fold lines define a pair of side panels which are folded against a central panel extending between said longitudinal fold lines. Each of the side panels has a longitudinally extending panel fold line which is adjacent to and spaced from its side edge. These longitudinally extending panel fold lines define a pair of edge panels which are folded back upon a portion of their respective side panels. The transversely folded drape may be shortened longitudinally, as seen in FIG. 6 of the patent, by ordinary fan-folding.

U.S. Pat. No. 3,881,476 discloses an interlocked surgical drape comprising a sheet having a plurality of longitudinally extending fold lines paralleling the side edges thereof. The sheet is fan-folded from each side edge toward the center to provide two stacks of folds which lie adjacent each other, this folding producing a first folded unit which is reduced in width. The first folded unit is then folded along a fold line in the mid-region thereof to define a pair of contiguous end portions which extend from the mid-region fold line and which have free ends. The contiguous end portions are then fan-folded a sufficient number of times to interleave them, thus interlocking the drape and preventing premature unfolding.

U.S. Pat. No. 3,998,221 discloses a drape assembly for a surgical equipment table, said drape comprising a set-up drape and a table drape. The table drape is fan-folded in both the transverse and lateral directions.

Sterile drapes of the aforementioned kind are usually applied to patients, instrument tables, operating room tables, and the like in preparation for surgery. The surgical drape, in addition to protecting the surgically prepared areas of the patient's skin from contamination, also protects surgeons and nurses and their operating room apparel against contamination through contact with unprepared or contaminated areas of the skin which might be a source of infection.

There are usually two kinds of nurses present in the operating room. One is referred to as the "scrub" nurse, that is, a nurse who has scrubbed and disinfected exposed areas of the skin, wears gloves, and is deemed to be sterile. The other kind of nurse present in the operating room is referred to as a circulating nurse, that is, a nurse who has not scrubbed, who does not wear gloves, and who is considered non-sterile. Sterile drapes and instruments may be handled by the scrub nurse without destroying their sterility. Items or surfaces which have been contacted by the circulating nurse, however, have the sterility destroyed and must either be replaced or used in such fashion that the surface which is contaminated (or deemed to be contaminated) will not be exposed. Thus, in the case of a sterile surgical drape, for example, it would be permissible for the circulating nurse to handle a particular area of the drape if the particular area so handled does not thereafter contact a sterile surface.

Advantageously, a drape folded in accordance with the present invention may be applied by a circulating (non-sterile) nurse without danger of contaminating an existing aseptic field (for example, the surgically prepared skin of a patient) over which it is placed. Additionally, the folded drape may be applied by the circulating nurse to, for example, a back table to provide a sterile surface on which other sterile items, such as drapes or equipment, may be placed without the danger of contaminating the same.

SUMMARY OF THE INVENTION

In accordance with the present invention, there is provided a surgical cover sheet or drape which has been folded to reduce its size. The drape can be applied by a circulating nurse to provide a sterile surface, as in the case where the drape is used to cover a back table.

In addition, the drape of the invention can be applied by the circulating nurse without danger of contaminating the aseptic field, e.g., the surgically prepared skin of a patient, to which it is applied. Since the drape may be safely applied by the circulating (non-sterile) nurse, the scrub (sterile) nurse is free to attend to other duties prior to surgery.

A surgical drape or cover sheet in accordance with the present invention is longitudinally shortened and comprises a sheet of flexible, drapable material, said sheet comprising a top edge, a bottom edge, a pair of opposed side edges, said sheet comprising nine sections, said first section lying between said bottom edge and a first line running transversely of said sheet, said second section lying between said first transverse line and a second line running transversely of said sheet, said third section lying between said second transverse line and a third line running transversely of said sheet, said fourth section lying between said third line and a fourth line running transversely of said sheet, said fifth section lying between said fourth line and a fifth line running transversely of said sheet, said sixth section lying between said fifth line and a sixth line running transversely of said sheet, said seventh section lying between said sixth line and a seventh line running transversely of said sheet, said eighth section lying between said seventh line and an eighth line running transversely of said sheet, and said ninth section lying between said eighth line and said top edge; the largest of said sections being said fifth section, said second and third sections being substantially equal in size, said fourth section being somewhat larger than said second and third sections, said first section being smaller than said second and third sections, said seventh and eighth sections being substantially equal in size, said sixth section being somewhat larger than said seventh and eighth sections, and said ninth section being smaller than said seventh and eighth sections; said sheet being initially forward folded around said third transverse line, then, in sequence, reverse folded around said second line, forward folded around said fourth transverse line, and reverse folded around said first transverse line to provide a first stack of folds overlying at least part of said fifth section; said sheet thereafter and in sequence being forward folded around said sixth transverse line, reverse folded around said seventh line, forward folded around said fifth line and reverse folded around said eighth line to provide a second stack of folds overlying at least part of said first stack of folds.

In accordance with another aspect of the invention the longitudinally folded surgical drape is folded in the transverse direction to provide a completely folded drape which is compact in size, readily packaged, and capable of being applied by the circulating nurse in the manner described above.

As used herein, a "forward fold" is a fold in which one portion of the upper surface of the drape is turned toward another portion of the upper surface of the drape around a specified fold line. This is illustrated in FIG. 2 of the accompanying drawings wherein that portion of the drape extending from bottom edge 15 to transverse fold line 33 has been forward folded around fold line 33. A "reverse fold" is a fold in which one portion of the lower surface of the drape is turned toward another portion of the lower surface of the drape around a particular fold line. This is illustrated in FIG. 3 wherein that portion of the drape extending from bottom edge 15 to transverse fold line 32 has been reverse folded around fold line 32.

BRIEF DESCRIPTION OF THE DRAWINGS

The invention will be more easily understood by referring to the accompanying drawings in which:

FIG. 2 is a perspective of the drape after the first folding step has been completed;

FIG. 3 is a perspective of the drape after the first and second folding steps have been completed;

FIG. 4 is a perspective of the drape after the first three folding steps have been completed;

FIG. 5 is a schematic cross-section taken along line 5—5 of FIG. 4;

FIG. 6 is a perspective of the drape after the first five folding steps have been completed;

FIG. 7 is a schematic cross-section taken along line 7—7 of FIG. 6;

FIG. 8 is a perspective of the drape after the first six folding steps have been completed;

FIG. 9 is a cross-sectional view taken along line 9—9 of FIG. 8;

FIG. 10 is a perspective of the drape after the first seven folding steps have been completed;

FIG. 11 is a perspective view of the drape after completion of all folding steps to shorten the drape longitudinally;

FIG. 12 is a schematic cross-section taken along line 12—12 of FIG. 11;

FIG. 13 is a plan view of the longitudinally folded drape of FIG. 1 and showing the vertically extending fold lines around which the drape is folded in the traverse direction;

FIG. 14 is a perspective of the drape of FIG. 11 after it has been partially folded in the transverse direction;

FIG. 15 is a perspective of the drape of the invention after the longitudinal and transverse folding steps have been completed; and FIG. 16 is a schematic cross-section taken along line 16—16 of FIG. 15.

Figure 1:
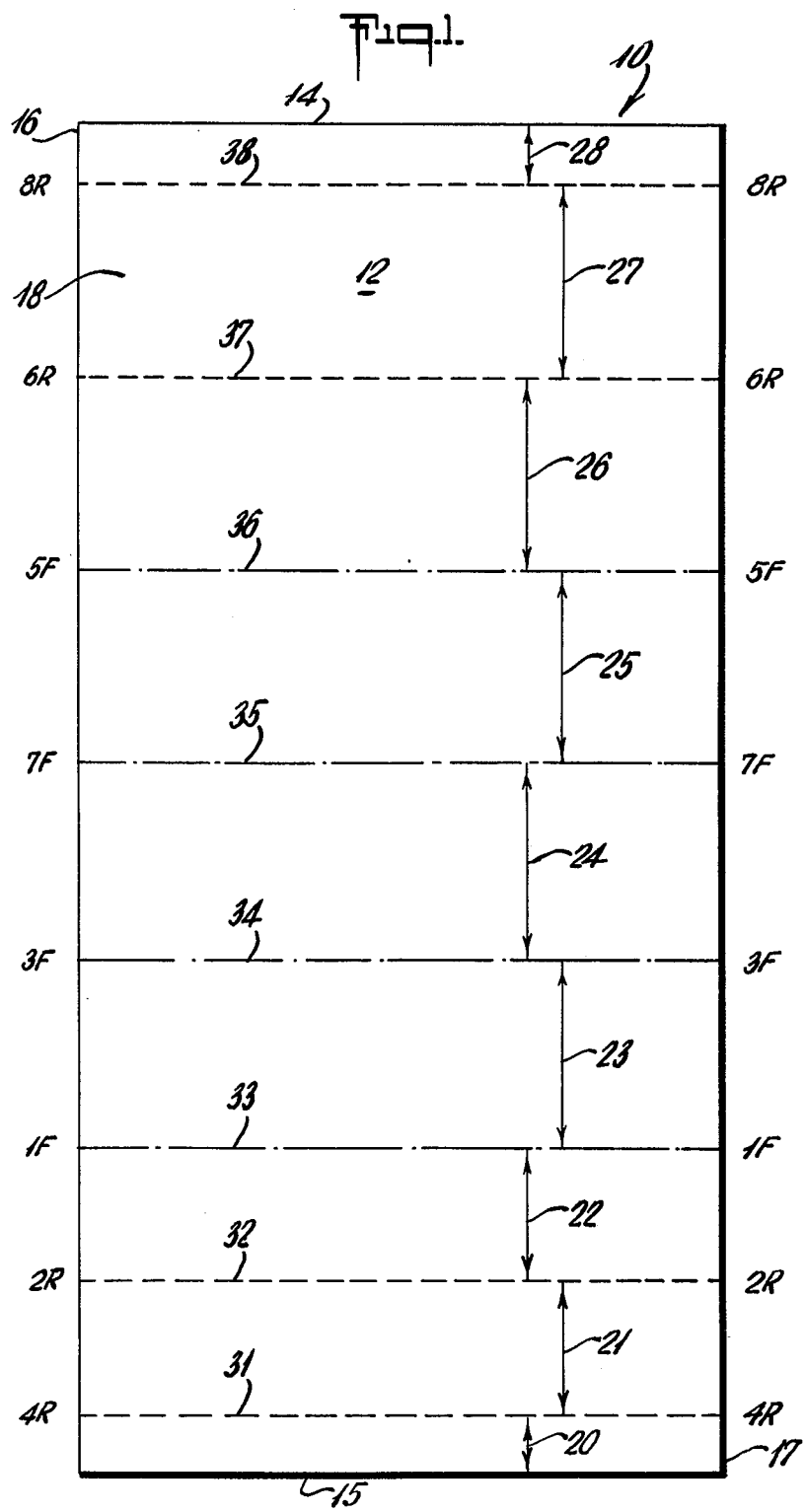
FIG. 1 is a top plan view of a surgical drape in accordance with the present invention and showing the horizontally extending fold lines along which the drape is folded.

Referring now to the drawings, and especially FIG. 1, there is shown a surgical drape 10 in a flat, unfolded configuration. Surgical drape 10 comprises a sheet 12 of flexible, drapable material which may be a woven fabric, a nonwoven fabric or a plastic film. Preferably, however, the drape comprises a nonwoven fabric which may be reinforced, if desired, with a lightweight scrim. The perimeter of drape 10 is defined by transversely extending top edge 14, longitudinally extending bottom edge 15, and a pair of longitudinally extending opposed side edges 16 and 17. Drape 10 has an upper surface 18 and a lower surface 19 (FIG. 2). Sheet 12 may be thought of as comprising a plurality of panels each having a pair of opposed edges defined by fold lines running transversely thereof. The fold lines are shown in the drawings in dot and dash form. In the preferred embodiment, drape 10 comprises nine transversely extending panels. First or lowermost panel 20 lies between bottom edge 15 and a first transverse fold line 31. Second panel 21 lies between first fold line 31 and a second transverse fold line 32. Third panel 22 lies between second fold line 32 and a third transverse fold line 33. Fourth panel 23 lies between third fold line 33 and a fourth transverse fold line 34. Fifth panel 24 lies between fourth fold line 34 and a fifth transverse fold line 35. Sixth panel 25 lies between fifth fold line 35 and a sixth transverse fold line 36. Seventh panel 26 lies between sixth fold line 36 and a seventh transverse fold line 37. Eighth panel 27 lies between seventh fold line 37 and an eighth transverse fold line 38. Finally, ninth or uppermost panel 28 lies between eighth fold line 38 and top edge 14 of the drape.

It has been ascertained that a folded surgical cover which is particularly suitable for covering instrument tables of the kind commonly referred to as back tables may be folded from a sheet of flexible material about 90 inches long and 44 inches wide. It will be understood, however, that the dimensions of the sheet may be varied without departing from the spirit and scope of the present invention, and that the surgical cover sheet may be used not only as a drape for tables and other kinds of operating room equipment but also as a patient drape.

Whatever the length of the starting sheet, panel 24 must have a length (as measured parallel to side edges 16, 17) which is at least slightly larger than the length of any of the remaining panels. Panels 23 and 25 have a smaller length than panel 24 and their lengths may differ one from the other. The length of panel 21 may be substantially the same as, but cannot be greater than, the length of panel 22. Panels 21 and 22 are smaller in length than panel 23. The length of panel 20 is preferably substantially less than that of panel 21. The length of panel 26 may be substantially the same as, but cannot be greater than, the length of panel 25. Preferably, however, the length of panel 26 is somewhat less than the length of panel 25. The length of panel 27 cannot be greater than the length of panel 26. The length of panel 28 is preferably considerably less than the length of panel 27. The total of the lengths of the plurality of panels is equal to the length, measured parallel to its side edges, of sheet 12. The width of each panel is equal to the width, measured parallel to top edge 14 and bottom edge 15, of sheet 12.

The drape is first folded to shorten it in the longitudinal direction, that is, in the direction which parallels opposed side edges 16, 17. The designations 1F, 2R, 3F . . . etc., appearing at the sides of drape 10 in FIG. 1 show the kind of fold and the sequence in which the folds are made. "F" indicates a forward fold and "R" indicates a reverse fold. The numbers 1, 2, 3 . . . etc., in these designations indicate the sequence in which the folds are made.

Referring to FIGS. 1 and 2, that portion of the drape between bottom edge 15 and third transverse fold line 33 is forward folded around fold line 33. After this step has been completed, the upper surface of that portion of the drape between bottom edge 15 and fold line 33 is in face-to-face contact with a part of the upper surface of the remainder of the drape.

The portion of the drape between bottom edge 15 and fold line 32 is then reverse folded around fold line 32 to give the partially folded drape shown in FIG. 3. It will be noted that, when this step is completed, the lower surface of that portion of the drape between fold lines 32 and 33 is in face-to-face contact with a part of the lower surface of that portion of the drape between fold line 32 and bottom edge 15.

In the third step, the drape is forward folded around transverse fold line 34 as indicated by the designation 3F to give the partially folded drape shown in perspective in FIG. 4 and in schematic cross-section in FIG. 5.

In the fourth step, first panel 20 is reverse folded around fold line 31 to give a partially folded drape in which the lower surface of panel 20 comes into face-to-face contact with a part of the lower surface of panel 23 (panel 23 being that portion of the drape lying between fold lines 33 and 34).

In the fifth step, that portion of the drape lying between fold line 36 and top edge 14 is forward folded around transverse fold line 36 to give the partially folded drape shown in perspective in FIG. 6 and in schematic cross-section in FIG. 7.

In the sixth step, that portion of the drape between fold line 37 and top edge 14 is reverse folded around line 37 to give the partially folded drape shown in perspective in FIG. 8 and in schematic cross-section in FIG. 9.

In the seventh folding step, the drape illustrated in FIGS. 8 and 9 is forward folded around transverse fold line 35 as indicated by the designation 7F. This gives the partially folded drape shown in perspective in FIG. 10.

The longitudinal folding is completed in the eighth step in which panel 28 (i.e., that portion of the drape between top edge 14 and fold line 38) is reverse folded around fold line 38. The completely longitudinally folded drape is shown in perspective in FIG. 11 and in schematic cross-section in FIG. 12. It will be observed that the longitudinally folded drape shown in FIGS. 11 and 12 comprises two stacks of folds. Both stacks of folds overlie panel 24, that is, both stacks overlie that portion of the drape between fold lines 34 and 35. The second stack of folds, that is, the stack of folds made by folding around fold lines 35, 36, 37, and 38 overlies the first stack of folds, that is, the stack of folds made by folding around fold lines 31, 32, 33, and 34.

After the drape has been folded longitudinally to reduce its length, it is folded transversely to reduce its width and provide a compact, longitudinally and transversely folded drape which is easily packaged and handled during use.

The longitudinally folded drape may be folded transversely in any number of ways to produce the completely folded drape. A preferred manner of folding the drape transversely is illustrated in FIGS. 13–15 of the drawings.

FIG. 13 shows the longitudinally folded drape of FIG. 11 marked with fold lines 9R, 10F, 11F, and 12F. The longitudinally folded drape comprises a generally centrally located intermediate portion 51 lying between fold lines 10F and 12F, a first end portion 52 lying between fold line 10F and side edge 16, and a second end portion 53 lying between fold line 12F and side edge 17. First end portion 52 comprises a major portion 52a lying between fold line 9R and 10F and a minor portion 52b lying between fold line 9R and side edge 16. Second end portion 53 comprises a major portion 53a lying between fold lines 11F and 12F and a minor portion 53b lying between fold line 11F and side edge 17. Major portion 52a must be larger than minor portion 52b and major portion 53a must be larger than minor portion 53b. Major portions 52a and 53a may differ in size from each other provided each is smaller than intermediate portion 51.

The first step in the transverse folding is to reverse fold minor portion 52b around fold line 9R after which major portion 52a is forward folded around fold line 10F. As seen in FIG. 14, these first two transverse folding steps are such that the upper surface of major portion 52a comes into contact with at least part of the upper surface of intermediate portion 51, while the lower surface of minor portion 52b contacts at least part of the lower surface of major portion 52a. The transverse folding is completed by forward folding minor portion 53b of second end portion 53 around fold line 11F and thereafter forward folding major portion 53a of second end portion 53 around fold line 12F. The completely folded drape is shown in perspective in FIG. 15 and in schematic cross-section in FIG. 16.

Surgical cover sheets in accordance with the present invention may be packaged and sterilized by the manufacturer. The folded drape is inserted into a suitable plastic or paper bag which is then sealed in any well known fashion. The packaged drape is then sterilized using e.g., steam, ethylene oxide or radiation techniques all of which are known in the art.

The drape is easily applied to an instrument table or a patient by unfolding it in the reverse sense in which it was folded. In draping a table, for example, the completely folded drape shown in FIG. 15 is placed on the table. The drape is grasped at fold line 11F (FIG. 15) and major portion 53 is unfolded so that the drape assumes the configuration shown in FIG. 14. The drape is then grasped at side edge 16 (FIG. 14) and unfolded to the position illustrated in FIGS. 13 and 11. The nurse then grasps panel 28 of the drape near its edge 14 (best seen in FIG. 11) and completely unfolds that portion of the drape lying between edge 14 and fold line 7F.

At this stage of the unfolding, the drape has assumed the partially folded configuration shown in FIG. 4, i.e., that portion of the drape lying between bottom edge 15 and transverse fold line 34 is still folded while the remainder, i.e., that portion lying between top edge 14 and fold line 34 is unfolded. Depending on the size of the table to which the drape is being applied, a portion of the drape adjacent edge 14 will hang over the edge of the table.

The unfolding is completed by the nurse's grasping panel 20 of the drape near its edge 15 (best seen in the lower right hand portion of FIG. 8) and pulling the drape over the other edge of the table. Again depending on the size of the table, a portion of the drape adjacent edge 15 will hang over the edge of the table. The table will now be completely draped.

It will be observed that the only parts of the drape which were either actually touched by the nurse or over which the nurse had to reach during the unfolding procedure were the following:

(a) the folded area in the vicinity of fold line 11F (FIG. 15);
(b) the area near side edge 16 and the lower surface of portion 52a (FIG. 14);
(c) panel 28 and the lower surface of panel 25 (FIGS. 11 and 12); and
(d) panel 20 and the lower surface of panel 23 (FIG. 8).

It will be observed that all portions of the drape listed in (a) through (d) immediately above are portions which are facing downwardly or which are below the table level when the table is completely draped. Thus, the sterility of that portion of the drape which overlies the table and faces upwardly is preserved during the draping procedure. Sterile instruments and the like may then be laid on top thereof without danger of their becoming contaminated.

What is claimed is:

1. Surgical drape comprising a sheet of flexible, drapable material, said sheet comprising a top edge, a bottom edge, a pair of opposed side edges, said sheet comprising nine sections, said first section lying between said bottom edge and a first line running transversely of said sheet,
said second section lying between said first transverse line and a second line running transversely of said sheet,
said third section lying between said second transverse line and a third line running transversely of said sheet,
said fourth section lying between said third line and a fourth line running transversely of said sheet,
said fifth section lying between said fourth line and a fifth line running transversely of said sheet,
said sixth section lying between said fifth line and a sixth line running transversely of said sheet,
said seventh section lying between said sixth line and a seventh line running transversely of said sheet,
said eighth section lying between said seventh line and an eighth line running transversely of said sheet,
and said ninth section lying between said eighth line and said top edge;
the largest of said sections being said fifth section, said second and third sections being substantially equal in size,
said fourth section being somewhat larger than said second and third sections,
said first section being smaller than said second and third sections,
said seventh and eighth sections being substantially equal in size,
said sixth section being somewhat larger than said seventh and eighth sections,
and said ninth section being smaller than said seventh and eighth sections;
said sheet being initially forward folded around said third transverse line, then, in sequence, reverse folded around said second line, forward folded around said fourth transverse line, and reverse folded around said first transverse line to provide a first stack of folds overlying at least part of said fifth sections;
said sheet thereafter and in sequence being forward folded around said sixth transverse line, reverse folded around said seventh line, forward folded around said fifth line and reverse folded around said eighth line to provide a second stack of folds overlying at least part of said first stack of folds.

2. A surgical drape according to claim 1 which is also folded transversely to provide a compactly folded drape.

3. A surgical drape according to claim 1, said drape comprising first and second end portions and an intermediate portion lying therebetween, said first and second end portions each having a major portion and a minor portion, one end of said intermediate portion adjoining the major portion of said first end portion along a first longitudinal line and the other end of said intermediate portion of said second end portion along a second longitudinal line; the major portion of said first end portion adjoining the minor portion of said first end portion along a third longitudinal line; the major portion of said second end portion adjoining the minor portion of said second end portion along a fourth longitudinal line; said drape being reverse folded around said third longitudinal line, forward folded around said first longitudinal line, forward folded around said fourth longitudinal line and forward folded around said second longitudinal line to provide a drape which is reduced in size in both the longitudinal and transverse direction.

* * * * *

UNITED STATES PATENT AND TRADEMARK OFFICE
CERTIFICATE OF CORRECTION

PATENT NO. : 4,185,625
DATED : January 29, 1980
INVENTOR(S) : Henrietta K. Morris It is certified that error appears in the above-identified patent and that said Letters Patent are hereby corrected as shown below:

Column 7, Line 55 : "It will be observed" should be --It will also be observed--.

Column 8, Line 56 : After the words "intermediate portion" and before the words "of said" should be inserted the words --adjoining the major portion--.

Signed and Sealed this

Third Day of June 1980

[SEAL]

Attest:

SIDNEY A. DIAMOND

Attesting Officer    Commissioner of Patents and Trademarks